(12) United States Patent
Reiner

(10) Patent No.: US 12,702,329 B2
(45) Date of Patent: Aug. 11, 2026

(54) END-USER IDENTIFICATION AND AUTHENTICATION UTILIZING IN VIVO SMART MEDICAL DEVICES

(71) Applicant: Bruce Reiner, Berlin, MD (US)

(72) Inventor: Bruce Reiner, Berlin, MD (US)

( * ) Notice: Subject to any disclaimer, the term of this patent is extended or adjusted under 35 U.S.C. 154(b) by 381 days.

(21) Appl. No.: 18/480,236

(22) Filed: Oct. 3, 2023

(65) Prior Publication Data

US 2024/0115167 A1 Apr. 11, 2024

Related U.S. Application Data

(60) Provisional application No. 63/414,186, filed on Oct. 7, 2022.

(51) Int. Cl.

*A61B 5/117* (2016.01)
*A61B 5/00* (2006.01)
*A61B 5/06* (2006.01)
*G16H 10/60* (2018.01)
*G16H 50/20* (2018.01)

(52) U.S. Cl.

CPC ............ *A61B 5/117* (2013.01); *A61B 5/0037* (2013.01); *A61B 5/061* (2013.01); *G16H 10/60* (2018.01); *G16H 50/20* (2018.01)

(58) Field of Classification Search

None

See application file for complete search history.

(56) References Cited

U.S. PATENT DOCUMENTS

| | | | | |
|---|---|---|---|---|
| 9,662,064 | B2 * | 5/2017 | Vilsmeier | A61B 5/4842 |
| 12,087,431 | B2 * | 9/2024 | Urness | G16H 40/67 |
| 12,211,151 | B1 * | 1/2025 | Chiou | G06T 19/003 |
| 2022/0304626 | A1 * | 9/2022 | Reiner | A61B 5/07 |
| 2023/0122851 | A1 * | 4/2023 | Urness | G16H 40/67 707/692 |

* cited by examiner

*Primary Examiner* — Darryl V Dottin

(74) *Attorney, Agent, or Firm* — Edwards Neils LLC; Jean C. Edwards, Esq.

(57) ABSTRACT

The present invention relates to a method of identification and localization of a device associated with a host, including: providing data on the device to an identification module from an imaging technology, a visualization technology, a remote sensing technology, or a device identifier; storing the data in a data storage; analyzing the data using the identification module; searching one of the data storage or a device database and cross-referencing the analyzed data with the device database; and identifying and localizing at least one of the device or the host using results of the cross-referenced search of the device database. A 2-D/3-D visualization map using a visualization module is used to provide a pictorial representation of the device. Artificial intelligence from an AI module is used to prepare the 2-D/3-D visualization map or analyze the data for localization and identification of the device.

23 Claims, 7 Drawing Sheets

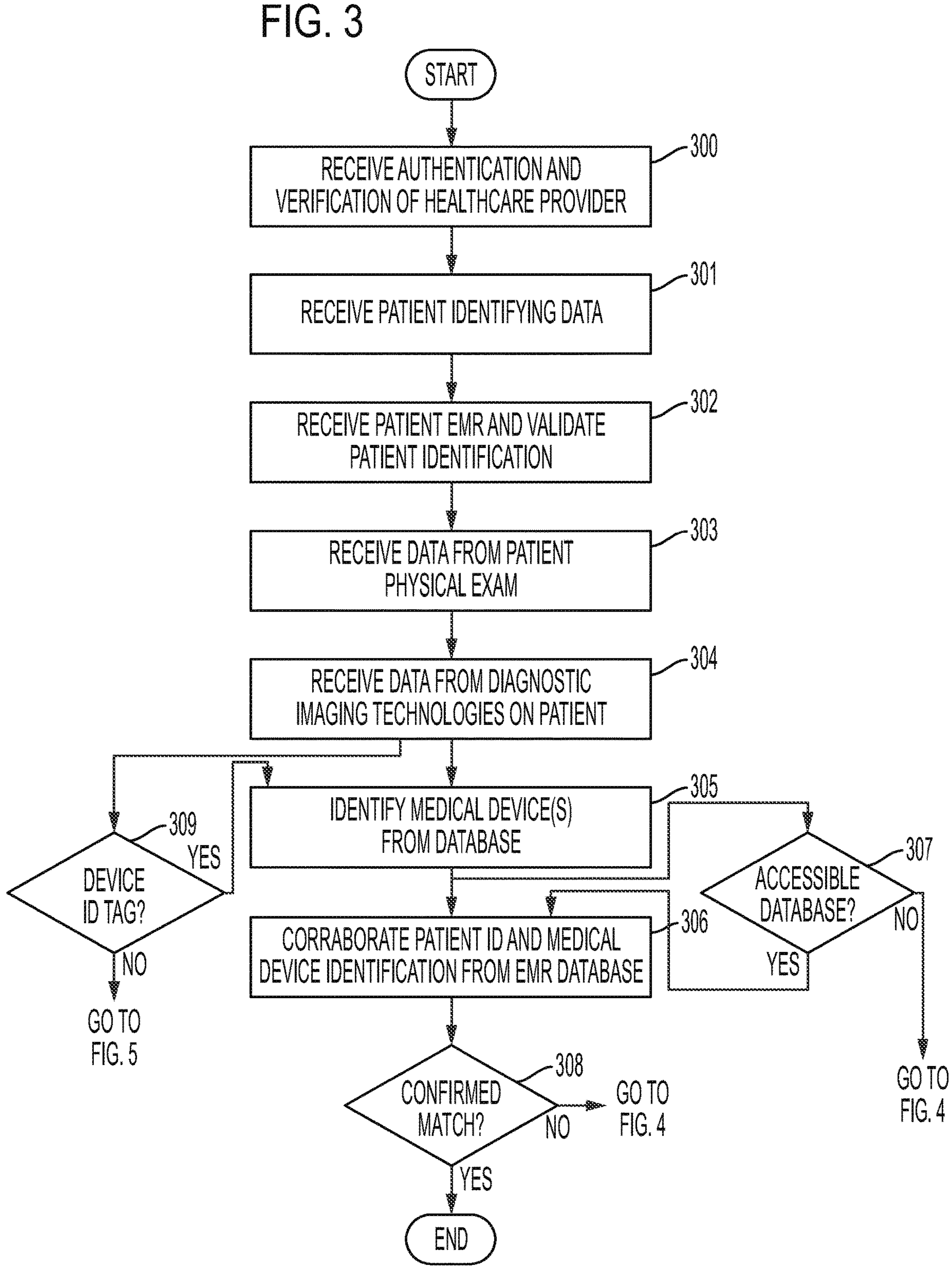
FIG. 3
START
RECEIVE AUTHENTICATION AND VERIFICATION OF HEALTHCARE PROVIDER
300
RECEIVE PATIENT IDENTIFYING DATA
301
RECEIVE PATIENT EMR AND VALIDATE PATIENT IDENTIFICATION
302
RECEIVE DATA FROM PATIENT PHYSICAL EXAM
303
RECEIVE DATA FROM DIAGNOSTIC IMAGING TECHNOLOGIES ON PATIENT
304
IDENTIFY MEDICAL DEVICE(S) FROM DATABASE
305
DEVICE ID TAG?
309
YES
NO
GO TO FIG. 5
ACCESSIBLE DATABASE?
307
NO
YES
GO TO FIG. 4
CORRABORATE PATIENT ID AND MEDICAL DEVICE IDENTIFICATION FROM EMR DATABASE
306
CONFIRMED MATCH?
308
NO
GO TO FIG. 4
YES
END

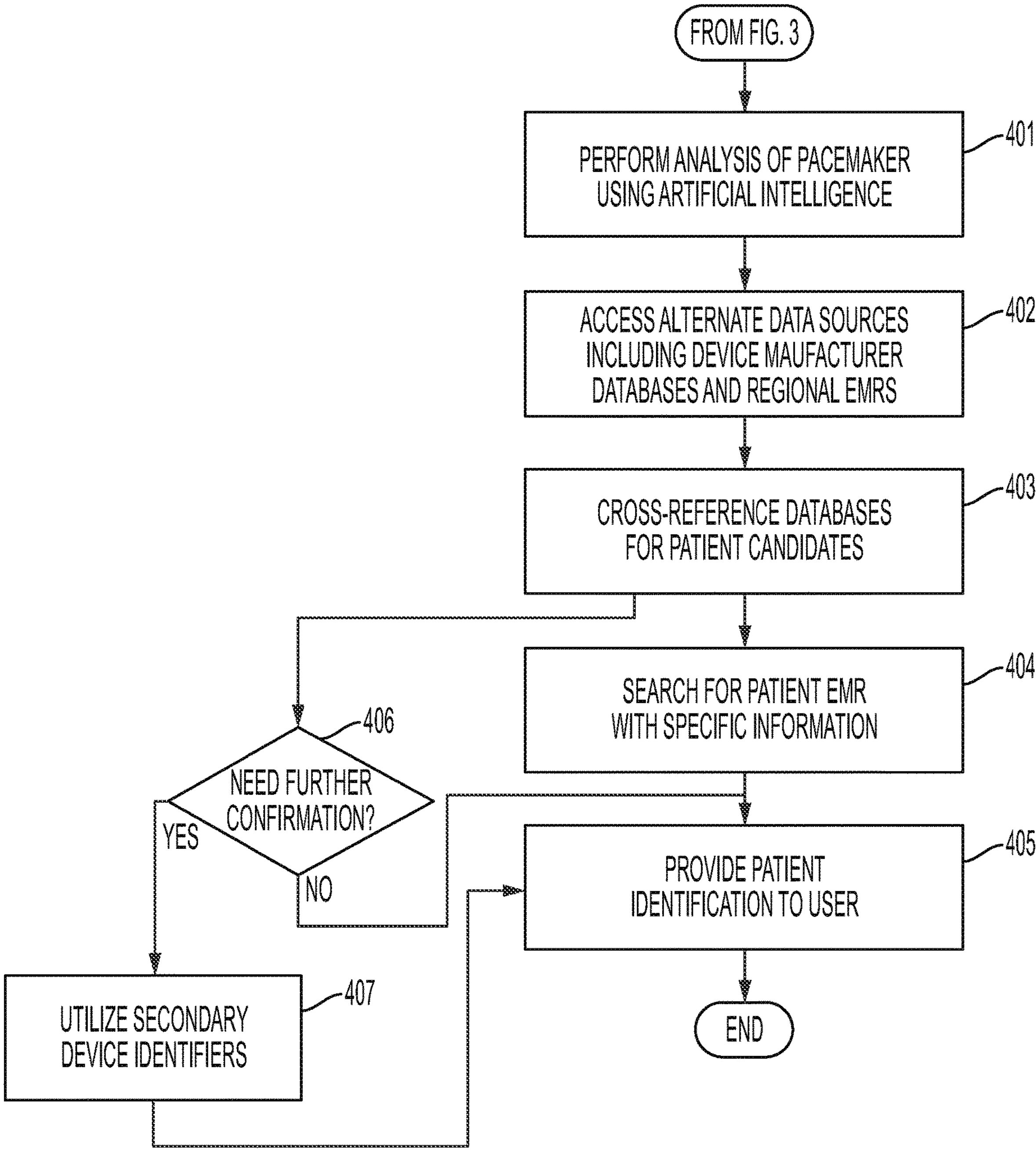
FIG. 4
FROM FIG. 3
PERFORM ANALYSIS OF PACEMAKER USING ARTIFICIAL INTELLIGENCE
401
ACCESS ALTERNATE DATA SOURCES INCLUDING DEVICE MAUFACTURER DATABASES AND REGIONAL EMRS
402
CROSS-REFERENCE DATABASES FOR PATIENT CANDIDATES
403
SEARCH FOR PATIENT EMR WITH SPECIFIC INFORMATION
404
406
NEED FURTHER CONFIRMATION?
YES
NO
PROVIDE PATIENT IDENTIFICATION TO USER
405
UTILIZE SECONDARY DEVICE IDENTIFIERS
407
END

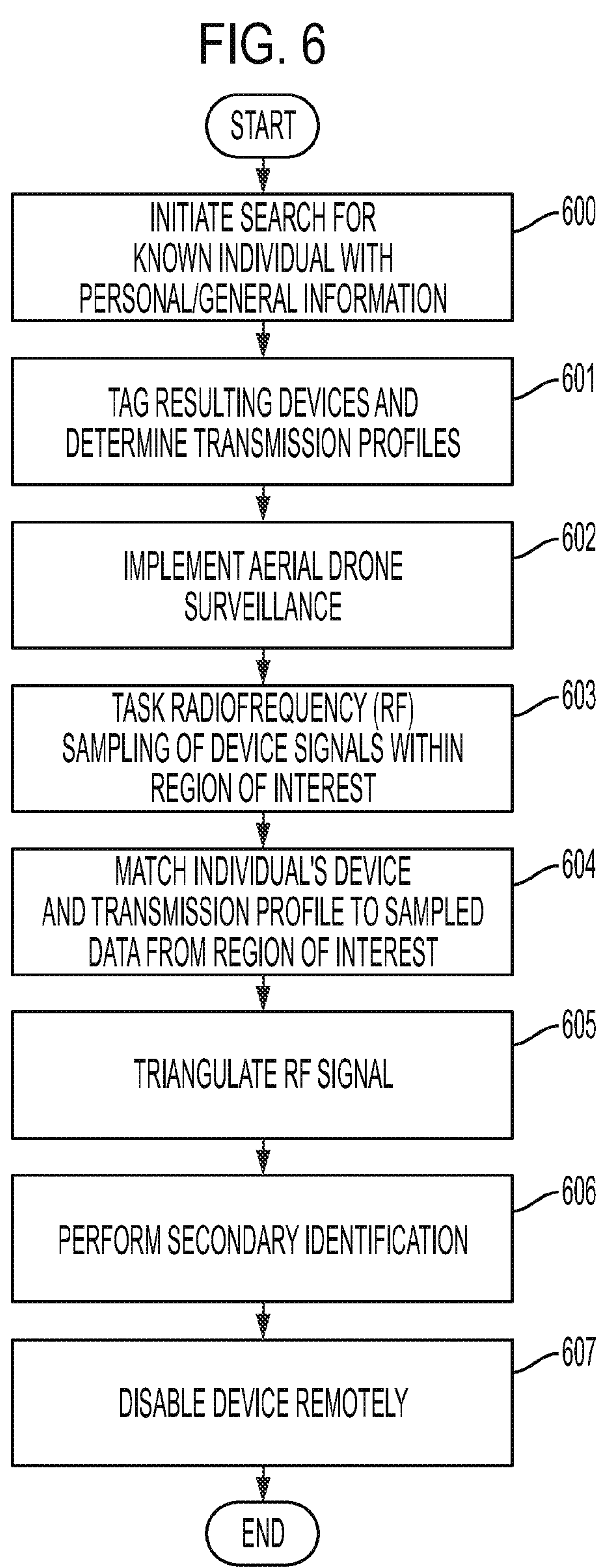
FIG. 6
START
INITIATE SEARCH FOR KNOWN INDIVIDUAL WITH PERSONAL/GENERAL INFORMATION
600
TAG RESULTING DEVICES AND DETERMINE TRANSMISSION PROFILES
601
IMPLEMENT AERIAL DRONE SURVEILLANCE
602
TASK RADIOFREQUENCY (RF) SAMPLING OF DEVICE SIGNALS WITHIN REGION OF INTEREST
603
MATCH INDIVIDUAL'S DEVICE AND TRANSMISSION PROFILE TO SAMPLED DATA FROM REGION OF INTEREST
604
TRIANGULATE RF SIGNAL
605
PERFORM SECONDARY IDENTIFICATION
606
DISABLE DEVICE REMOTELY
607
END

END-USER IDENTIFICATION AND AUTHENTICATION UTILIZING IN VIVO SMART MEDICAL DEVICES

CROSS-REFERENCE TO RELATED APPLICATIONS

The present invention claims priority from U.S. Provisional Patent Application No. 63/414,186 filed Oct. 7, 2022, the contents of which are herein incorporated by reference in their entirety.

BACKGROUND OF THE INVENTION

1. Field of the Invention

The present invention relates to the ability of an individual medical device, such as an in vivo smart medical device and/or its subcomponents, to take into account, a variety of unique medical device identifiers and attributes to create its own unique identification profile, which is in some respects analogous to biometrics markers, like a fingerprint. By cataloguing these device-specific variables, one can effectively create an objective and data-driven system in which medical devices can be used to identify and/or authenticate their individual host, which can exist in both human and computer forms.

2. Description of the Related Art

Medical devices have become an integral and essential component of modern healthcare, the importance of which will only continue to expand as patient populations progressively age and medical technologies continue to advance in scope and functionality.

A number of current and future trends exist in the medical device industry including (but not limited to) enhanced cybersecurity, wearable technologies, Internet of Medical Things (IoMT), robotics, genomics, 3-D printing, and enhanced connectivity. Medical devices will continue to get smaller, faster, and more flexible, while increasing in efficiency, communication, and functionality. As the reliance and dependability of medical devices continues to expand in both diagnostic and therapeutic applications, so too will their overall number, diversity, and complexity.

While medical devices have traditionally been thought of in their implanted forms, new generations of medical devices are taking shape, transforming their locations, forms, composition, and portability. With increasing options for medical device architecture, new innovation opportunities can be created, in which medical devices take on new roles in which they have not traditionally been associated with. One of these novel applications is described in this patent.

As medical device implementation continues to expand, their representation will begin to encompass the entire host populations and redefine each individual host's identity and profile. In this expanding technologically driven world, medical devices can define the individual end-user in which they reside, while simultaneously each individual end-user can be defined by the medical devices which maintain homeostasis within their dynamic biologic systems.

A number of strategies are currently available for establishing and/or verifying an individual person's identity. Some of the more commonly used strategies include (but are not limited to) token-based identification (e.g., passports, driver's license), knowledge-based identification (e.g., passwords, personal identification numbers), and biometrics. Biometrics include biologic data in the form of measurements and calculations related to individual human characteristics (e.g., fingerprints, facial recognition, iris recognition). An alternative to biometrics is behavior-metrics, which relate to an individual person's patterns of behavior (e.g., computer mouse movements, typing rhythm, gait), which collectively can be used to create behavioral profiles. Since biometrics have recently become the de facto standard for identification and/or authentication, this provides a contrast to the present invention.

A fundamental prerequisite to the widespread use of biometrics is the creation of a comprehensive database. This has currently been created in the United States under the direction of the Department of Homeland Security (DHS) and the Office of Biometrics Identity Management (OBIM). The resulting biometrics data repository is called the Automated Biometrics Identification System (IDENT), which contains over 260 million unique identifiers.

This capability of identifying and authenticating computer subjects is extremely important in current and future environments, in which automation, robotics, and artificial intelligence will become more prevalent in everyday life. Without robust and verifiable methods for establishing computer identification and authentication, cybersecurity concerns could prove to be catastrophic.

It is worth noting that underlying efforts to create such databases are already in place under the direction of the Food and Drug Administration (FDA). In 2007, the U.S. Congress mandated medical device manufacturers (MDMs) create a unique identifying number for each specific product, akin to a vehicle indentation number (VIN) on automobiles. In 2015, the FDA adopted the final rules regarding medical device identification requirements.

Currently, MDMs are required to include a unique device identifier (UDI) on the label of all implantable and life supporting/life sustaining medical devices. As of September 2022, UDIs will also be required for lower risk/non-implantable devices.

These UDIs are meant to be readable as well as scannable, while containing 62 individual data elements initially, including the manufacturer name, device name, and device model number. This information will be stored in the Access Global Unique Device Identification Database (Access GUDID), a publicly accessible database maintained by the FDA.

Similar efforts at establishing different types of medical device databases are also underway in other countries including (but not limited to) the International Medical Devices Database (covering 26 countries) and Medical Device Information System (MDIS) in the United Kingdom, along with a variety of industry sponsored initiatives.

While the primary intent of these efforts is focused on longitudinal analysis of medical device complications and potential product recalls, the foundations being established create the potential for larger and more comprehensive medical device databases to support alternative methodology for host subject identification and authentication.

SUMMARY OF THE INVENTION

The present invention relates to the ability of an individual medical device, such as an in vivo smart medical device and/or its subcomponents, to take into account, a variety of unique medical device identifiers and attributes to create its own unique identification profile, which is in some respects analogous to biometrics markers, like a fingerprint.

By cataloguing these device-specific variables, one can effectively create an objective and data-driven system in which medical devices can be used to identify and/or authenticate their individual host, which can exist in both human and computer forms.

The present invention creates a database, comparable to the present MDIS database, for identification/authentication, but replaces biometric data with technologic data attributed to medical devices, in their various forms, structures, and functionality. But unlike biometrics, which is specific to the identification/authentication of human subjects, the present invention creates the ability to be applied to both human and machine subjects (e.g., computers), which will subsequently be referred to as hosts.

In one embodiment, a method of identification and localization of a device associated with a host, includes: providing data on the device to an identification module from at least one of an imaging technology, a visualization technology, a remote sensing technology, or a device identifier; storing the data in a data storage; analyzing the data using the identification module; searching one of the data storage or a device database and cross-referencing the analyzed data with the device database; and identifying and localizing at least one of the device or the host using results of the cross-referenced search of the device database.

In one embodiment, the method further includes: preparing a two-dimensional (2-D)/three-dimensional (3-D) visualization map or pictorial representation of the device using a 2-D/3-D visualization module, the 2-D/3-D visualization map which is unique to the host.

In one embodiment, the 2-D/3-D visualization map is provided to the identification module for the cross-referenced search.

In one embodiment, the method further includes: using artificial intelligence (AI) from an AI module to prepare said 2-D/3-D visualization map or analyze the data for localization and identification of the device.

In one embodiment, the data storage includes at least one of an internal data storage to the device, an external computer data storage, or an external database; and the external database includes local, regional, and international databases.

In one embodiment, the device identifiers include at least one of: device identification tags, device embedded microchips, device quality assurance (QA)/quality control (QC) testing, device imagery, patient-specific medical data, the 2-D/3-D visualization map, a device motion map, a device transmission profile, inter-device communication, device anatomic location, device functionality, device structural integrity, device individual and/or grouped components, device-specific data, device performance metrics, synergistic devices, or device architecture.

In one embodiment, the imaging technology includes at least one of X-ray, computed tomography (CT), ultrasound, nuclear medicine, or magnetic resonance imaging (MRI).

In one embodiment, the visualization technology includes at least one of thermal, vibration, sound emission, or light measuring technology.

In one embodiment, the device motion map is acquired in real-time and cross-referenced with the device database to identify the device and the host.

In one embodiment, age-adjusted modeling of appearance of the device is performed to predict changes in the device appearance over time.

In one embodiment, remote sensing technologies include at least one of drones, satellites, closed-circuit television (CCTV) or infrared lasers.

In one embodiment, the device includes an internal activation sensor which emits a signal that is detected by a signal detector and provided to at least one of said identification module or the 2-D/3-D visualization map module.

In one embodiment, the signal includes at least one of laser, ultrasound, electromagnetic radiation, radiofrequency (RF), infrared light, thermal energy, sound, or vibration.

In one embodiment, the device embedded microchips are capable of being selectively turned on and off by authorized third parties when the host or the device requires localization.

In one embodiment, identification and localization of the host is implemented on condition that the host travels beyond a predefined geographic area or the host is in imminent danger based on a plurality of predetermined threshold criteria.

In one embodiment, an apparatus which identifies and localizes a device associated with a host, includes: an identification module which receives data on the device from at least one of an imaging technology, a visualization technology, a remote sensing technology, or a device identifier; a data storage which stores the data; wherein the identification module analyzes the data using the identification module, and cross-references the analyzed data with a device database; and wherein at least one of the device or the host is at least one of identified or localized using results of the cross-referenced search of the device database.

In one embodiment, a method of identifying a patient, includes: receiving data from a device by at least one of an imaging technology, a visualization technology, a remote sensing technology, or a device identifier; obtaining personal identifying information of the patient and storing the identifying information in a data storage; receiving medical data on the patient from a patient examination; providing the data from the device and medical data from the patient to an identification module, which accesses the data storage and locates identification data on the patient; providing said identification data on the patient to a user; accessing an electronical medical record (EMR) on the patient to validate the identification of the patient and to retrieve patient medical records; corroborating the identification of the patient with the patient medical records at the identification module; and confirming the identification of the patient.

In one embodiment, on condition that the EMR is not accessible, at least one of an imaging technology, a plurality of alternative databases, or secondary device identifiers are utilized to provide information to the identification module in place of patient medical records; and artificial intelligence is used by an artificial intelligence module to analyze the information and confirm the identification of the patient.

In one embodiment, a method of identifying at least one individual based on a device associated with the at least one individual, includes: searching a region of interest for signals emitted by the device associated with the at least one individual, using at least one of an imaging technology, a visualization technology, a remote sensing technology, or a device identifier; matching the signals emitted from the device with the identifying data on the device at an identification module; determining a location of the at least one individual based on the signals emitted from the device using the identification module; implementing a secondary form of identification of the at least one individual including at least remote sensing technologies or visualization technologies; and confirming the identification and the location of the at least one individual.

In one embodiment, an identification of the at least one individual is predetermined, and information on the at least one individual and the device are obtained and used in the searching step.

In one embodiment, the at least one individual is a plurality of individuals.

In one embodiment, the identification module analyzes the signals of the plurality of individuals and distinguishes a status between alive and deceased individuals and prioritizes alive individuals.

In one embodiment, EMRs are obtained on the plurality of individuals and provided to healthcare providers along with location and identification of the alive individuals.

Thus, has been outlined, some features consistent with the present invention in order that the detailed description thereof that follows may be better understood, and in order that the present contribution to the art may be better appreciated. There are, of course, additional features consistent with the present invention that will be described below, and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The description of the drawings includes exemplary embodiments of the disclosure and are not to be considered as limiting in scope.

FIG. 3 is a flow chart of a standard workflow method of confirming a patient identity, according to one embodiment consistent with the present invention.

FIG. 4 is a flow chart of a method of identifying a medical device, with a non-accessible device database, according to one embodiment consistent with the present invention.

FIG. 6 is a flow chart of a method of remote identification of a known individual according to one embodiment consistent with the present invention.

DESCRIPTION OF THE INVENTION

The present invention relates to the ability of an individual medical device, such as an in vivo smart medical device and/or its subcomponents, to take into account, a variety of unique medical device identifiers and attributes to create its own unique identification profile, which is in some respects analogous to biometrics markers, like a fingerprint. By cataloguing these device-specific variables, one can effectively create an objective and data-driven system in which medical devices can be used to identify and/or authenticate their individual host, which can exist in both human and computer forms.

The present invention creates a database, comparable to the present MDIS database, for identification/authentication, but replaces biometric data with technologic data attributed to medical devices, in their various forms, structures, and functionality. But unlike biometrics, which is specific to the identification/authentication of human subjects, the present invention creates the ability to be applied to both human and machine subjects (e.g., computers), which will subsequently be referred to as hosts.

A. Description of the Computer System of the Invention

Figure 1:
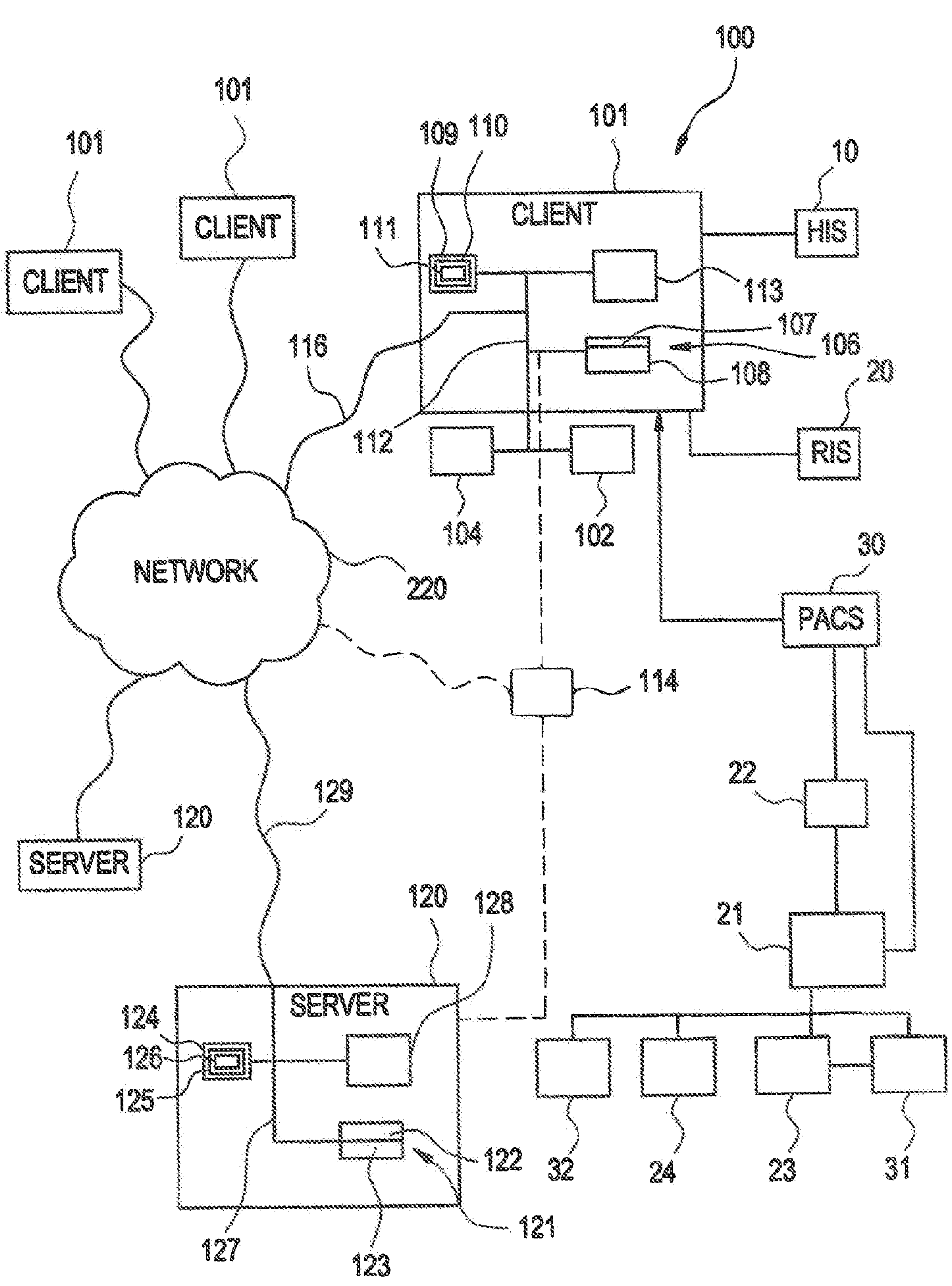
FIG. 1 is a block diagram of a computer system and its components, according to one embodiment consistent with the present invention.

According to one embodiment of the invention illustrated in FIG. 1, medical applications may be implemented using the system 100. The system 100 is designed to interface with existing information systems such as a Hospital Information System (HIS) 10, a Radiology Information System (RIS) 20, a radiographic device 21, and/or other information systems that may access a computed radiography (CR) cassette or direct radiography (DR) system, a CR/DR plate reader 22, a Picture Archiving and Communication System (PACS) 30, and/or other systems. The system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the system 100 of the present invention and the information systems, such as the HIS 10, RIS 20, QA sensor device 21, CR/DR plate reader 22, and PACS 30, etc., may be enabled to allow the system 100 to retrieve and/or provide information from/to these systems. According to one embodiment of the invention, bi-directional communication between the system 100 of the present invention and the information systems allows the system 100 to update information that is stored on the information systems. According to one embodiment of the invention, bi-directional communication between the system 100 of the present invention and the information systems allows the system 100 to generate desired reports and/or other information.

The system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), tablet, smart phone, or other mobile terminals that are operated by the user accessing the program 110 remotely.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, or other input device 104.

According to one embodiment of the invention, the input or other selection device 104 may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection.

According to another embodiment of the invention, symbols and/or icons may be entered and/or selected using an input device 104, such as a multi-functional programmable stylus. The multi-functional programmable stylus may be used to draw symbols onto the image and may be used to accomplish other tasks that are intrinsic to the image display, navigation, interpretation, and reporting processes. The multi-functional programmable stylus may provide superior functionality compared to traditional computer keyboard or mouse input devices. According to one embodiment of the invention, the multi-functional programmable stylus also may provide superior functionality within the PACS and Electronic Medical Report (EMR).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the image display device 102 may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the system 100 may include separate programs 110 having code that performs desired operations. According to one embodiment of the invention, the program 110 that runs the system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, the system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines.

According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, and the PACS 30 (if separate) are shown as directly coupled to the client computer 101, it is known that these systems may be indirectly coupled to the client over a LAN, WAN, the Internet, and/or other network via communication links. According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, or other forms of ROM or RAM either currently known or later developed. Further, although specific components of the system have been described, one skilled in the art will appreciate that the system suitable for use with the methods and systems of the present invention may contain additional or different components.

B. Description of the Invention

The present invention describes in detail a number of identification data elements which can be applied to medical devices, in both current and future forms. These device-specific identifiers can in turn be recorded and stored in local, regional, national, and/or international databases for the purpose of real-time host identification and authentication.

Figure 2:
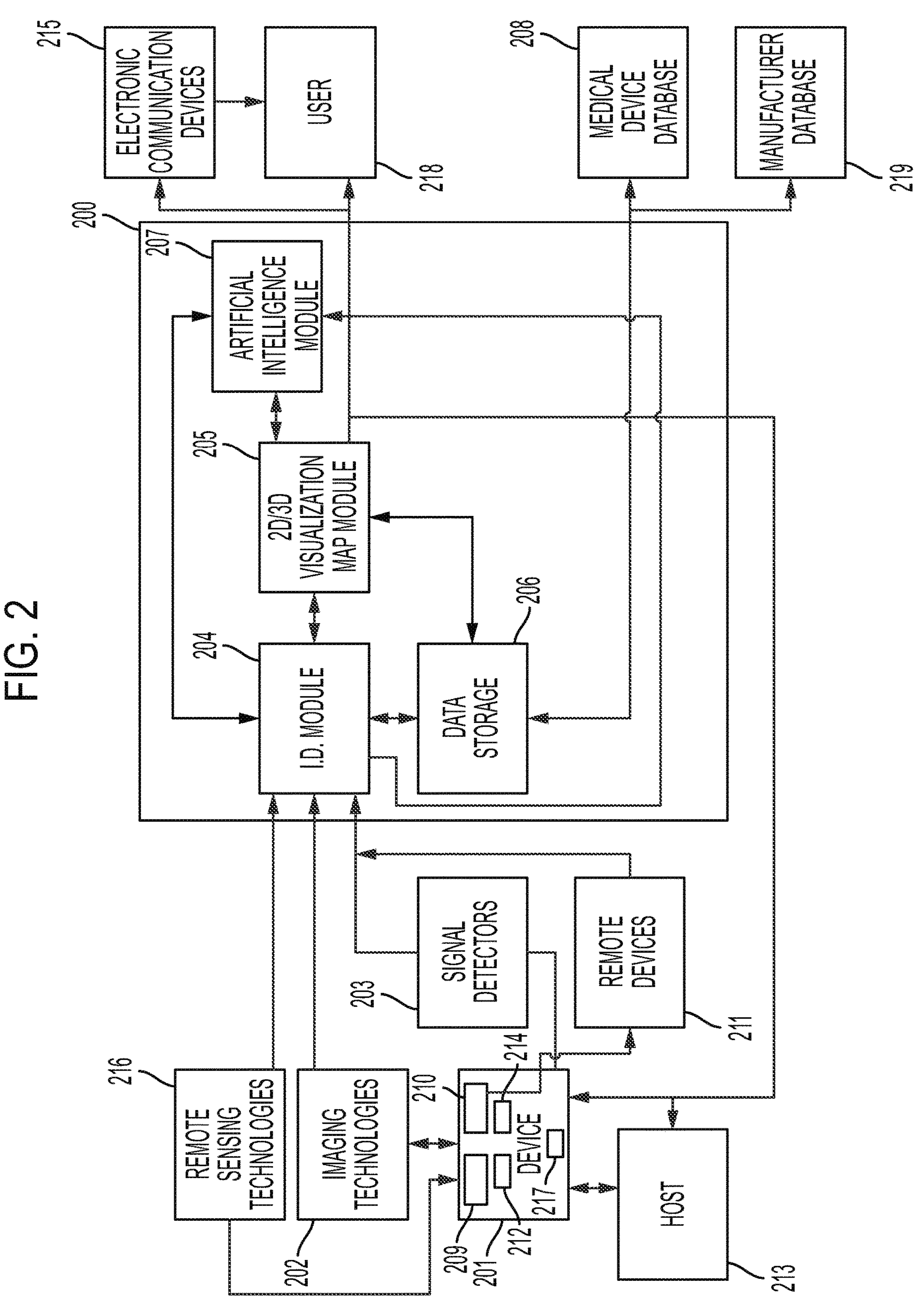
FIG. 2 is a schematic diagram of major components of the components of the computer system, according to one embodiment, consistent with the present invention.

It is important to note that the data and methodology used for host identification/authentication can manifest itself in a variety of ways, creating a dynamic and redundant system, which is difficult to circumvent. The data components used for identification/authentication can be solitary or multiple, nearby or remote, static or dynamic, adaptive or non-adaptive. As the complexity and number of variables in the device identifying data increases, so does the sensitivity and specificity of the identification/authentication process.

a. Medical Device Identifiers:

FIG. 2 shows a schematic diagram of the present invention and how the task of device 201 identification is performed. The processor 200 contains a number of components that accomplish this identification. Note that the processor 200 and its components can be contained in an external device (i.e., computer system 101 of a hospital, for example) or can be internal to the device 201 (i.e., in a host body 213), or contained within a remote system (i.e., remote sensing technology 216) etc., as the situation demands.

The various data which can be used for device classification and identification include (but are not limited to) the items listed below:

1. I.D. tags (e.g., Alpha numeric identifiers for both the device and its individual subcomponents).
2. Imagery.
3. Transmission profile.
4. Inter-device communication.
5. Anatomic location (fixed or dynamic).
6. Device Functionality (i.e., performance profile).
7. Structural integrity+/−defects.
8. Individual and/or grouped subcomponents (size, number, type, location, functionality, morphology).
9. Device-specific data (derived, transmitted, stored, transmitted, received).
10. Performance metrics (what specific functions does it perform, QA/QC issues).
11. Synergistic devices (if applicable).
12. Device Architecture (Map of subcomponents).

Identification (I.D.) tags or markers are currently in use by the FDA in which unique device identifiers (UDIs) are assigned to applicable medical devices, with incorporation of the following data:

1. Device Identifier (Manufacturer, Model, Version).
2. Production Identifier (Location and date of manufacture, Serial number, Expiration date, Distinct Identification Code (for human cell, tissue, or cellular/tissue-based products which are regulated as devices).

The corresponding data are subsequently used in the creation of a Global Unique Device Identification Database (GUDID) which catalogs each device with its own UDI. The present invention utilizes this existing data and expands it by a variety of additional device and host-specific identifying data, as listed below.

1. Primary Device (Manufacturer Name, Model, Version, Identification Number, Manufacturer Location, Manufacture Date, Expiration Date, FDA Data [if applicable]).
2. Secondary Devices (Same as Primary Device).
3. Implementation (Provider Name/s, Location, Institution (if applicable), Date and Time, Anatomic Location, Complications (if applicable).
4. Host (Name, Demographic Data, Clinical Indication, Primary and Secondary Diagnoses, Authorized Clinical Providers, Emergency Contact/s, Medical/Surgical History, Other Devices).
5. Functionality (Anatomic Location, Positional Variability, Transmission Profile, Communication Protocols, Security Features, Quality Assurance and Control, Pertinent Data).
6. Related Devices (Same as Primary Device, Data Exchange, Anatomic Location/s, Communication Protocols).
7. Visualization (Imagery, Device Architecture [Roadmap], Signal Output, Functional Analysis).

An important concept requiring consideration is that as medical devices will continue to undergo evolutionary change, so too will the number and uniqueness of identifying data. One relevant example of an entirely new class of device-specific identifying data was described by this inventor, in U.S. Provisional Patent Application No. 63/394,823, filed Aug. 3, 2022, U.S. Pat. No. 11,324,451, and U.S. patent application Ser. No. 17/836,742, filed Jun. 9, 2022, all of which are herein incorporated by reference in their entirety—in which a variety of bio sensors and miniaturized components can be directly embedded into medical device structure. With this development comes an entirely new class of device I.D. data, which will dramatically expand device individuality and specificity. Eventually, it is entirely possible that future device identification schema will create an identification system similar to fingerprints, where no two devices are identical to one another.

As noted above, imagery provides another method for device 201 identification (i.e., imaging technologies 202). For superficial or wearable devices, photography or video serves as a readily available imaging method. Devices 201 which are internally located (i.e., in vivo) can be imaged using a variety of existing imaging technologies including (but not limited to) x-ray, CT, ultrasound, nuclear medicine, or MRI.

In addition to these conventional imaging technologies, alternative forms of visualization can be applied to the task of device identification using identification module 204, including (but not limited to) thermal, vibration, sound emission, and light measuring technologies (i.e., via signal detectors 203).

Regardless of the visualization technology used, the same principles apply. In one embodiment, once the identification module 204 receives all the signals and data (which are stored in data storage 206), the two-dimensional (2D)/three-dimensional (3-D) visualization module 205 creates a 2D/3D visualization map of the medical device 201 in question, which can be cross-referenced using artificial intelligence (AI) from an AI module 207 (e.g., convolutional neural networks, feature extraction, histogram of oriented gradients) with a medical device database 208 (external or internal) for analysis and identification.

In its most common form, imagery is thought of as creating a 2D or 3D pictorial representation of the physical device structure in its entirety. Imagery can also be used to create pictorial representations of device subcomponents, which in themselves can also be individually catalogued into standardized medical device databases and used for device identification/authentication. As an example, existing automatic implantable cardioverter defibrillator (AICD) devices include a pulse generator, leads, electrodes, and battery. Any one of these components can be imaged and used for identification purposes.

However, imagery need not be limited to physical representations of medical devices and/or subcomponents alone. Other forms of device-specific imagery can also be created that are based upon device function and physiology, rather than physical structure. Examples include visualization models for motion with a cardiac valve prosthesis, electrical signals with brain implants or an AICD, infusion maps with insulin and intrathecal drug pumps, and pressure and flow vectors with an endotracheal tube (ET tube) or vascular stent.

In these exemplary embodiments, functional maps can be created by the identification module 204 of the present invention based on physiologic (or pathologic) measurements intrinsic to the device and the anatomy in which it is located. Since these measurements change over time, and often in predictable patterns, the 2D/3D visualization map module 205 can effectively create visualization maps which can be catalogued by the program (i.e., data storage 206) and used as identifiers. In addition to being specific to the individual device and anatomy, in many cases these maps are unique to the individual host, due to a myriad of factors including (but not limited to) age, health status, underlying pathology, organ/body size, and age and condition of the device.

In one exemplary embodiment, the motion map for an aortic valve prosthesis has a unique characteristic waveform due to the underlying host's regurgitant flow. The magnitude and directionality of this flow is both predictable and specific to the individual host, and as such, specific to the individual aortic valve prosthesis. In one embodiment, a motion map of the device 201 can be acquired in real-time and cross referenced by the program with a standardized device database 206, 208, both the individual medical device and host patient could be identified and/or authenticated by the program. Thus, in one embodiment, these device-specific functional and/or physiologic maps can be used for the purpose of device identification and/or authentication (see FIGS. 3-7, for example), just like traditional imaging can be used.

In one embodiment, since devices 201 can sometimes be modified in appearance and/or function over time, these changes can be documented through periodic updates by the program within the data storage 206, 208. In the event that a significant change was to occur and go undocumented in the database 206, 208 by the program, this can serve as a potential source for misidentification and must therefore be accounted for by the program in the overall device identification statistical analysis (see FIG. 2).

In one exemplary embodiment, imagery is performed using an imaging device 202, of an inferior vena cava filter (IVC), which was inserted six years earlier. The image within the standardized database 206 from this same host was obtained at the time of insertion, but now shows a minor, yet recognizable change in one of the device 201 struts. As a result, upon the program analysis, the identification of this device 201 falls below an acceptable threshold predetermined by the user/program, for an unequivocal match.

However, in the exemplary embodiment, the device 201 in question has a well-documented history of device 201 wear, which when the program accounts for the specific make, model, and duration, matches the observed device strut wear. Using age-adjusted modeling (akin to age-adjusted pictures of a wanted criminal), the program can modify the overall device 201 appearance of the original device and accurately predict minor changes in appearance and display them to the user 218 (FIG. 2), and the program can now produce a higher statistical match.

In the exemplary embodiment, while a second data identifier would most likely be required by the program for definitive identification, this illustrates how temporal and undocumented changes can undergo statistical and computerized modeling by the program of the present invention, to enhance the accuracy of identification.

In one embodiment, the imaging technologies 202 which can be used for device 201 identification and/or authentication by the program, act in close proximity to the host subject. But in other embodiments, the host subject may be remotely located, prohibiting conventional imaging technologies for device identification. Such an occurrence may occur when the host subject is not aware or is noncompliant with the identification/authentication process. In such a circumstance, technology is required which can accurately identify the device from a distance, which may exceed the capabilities of traditional imaging technologies.

In one embodiment, the types of technologies 202 which may be used by the program for remote visualization include (but are not limited to) drones, satellites, and closed-circuit television (CCTV). Since the number of host subjects within a given image may be extremely large in number, it is important that the program has a method for selecting the specific host of interest from the large numbers of other potential host subjects.

In an exemplary embodiment where the devices of a targeted host have been previously established and documented, one method for identifying the targeted host within a crowd is to trigger an internal activation sensor 209 (i.e., akin to a transponder) from within a targeted host medical device 201. Once activated, an emitted signal can be detected by signal detector 203, the signals provided to the identification module 204, and localized by the remote visualization technology (i.e., visualization map module 205) of the program, to identify the targeted host.

In one embodiment, a wide array of emitted signals can be transmitted by the activated device 201 which may include (but not limited to) laser, ultrasound, electromagnetic radiation, infrared light, thermal energy, sound, and vibration. The corresponding receiving technology (i.e., subsequent to detectors 203) would include the remote visualization technology (i.e., identification module 204 and visualization map module 205), allowing for the emitted signal to be received, processed, analyzed and localized by the program (see FIG. 2 and FIGS. 3-7, for example).

In one embodiment, there may be conditions where the target host medical devices 201 are not capable of being remotely activated, which effectively prohibits selective identification of the target host from the myriad of surrounding people in the crowd. However, if the host target's medical devices 201 have previously been enrolled in the medical device database of the present invention, there is pre-existing knowledge as to the specific number, type, and anatomic locations of medical devices 201 within the host subject (see FIG. 5).

In one embodiment, since the target host 213 is being identified through remote technologies, the ability to directly visualize the in vivo medical devices 201 using traditional visualization technologies is not practical. Instead, one must create technology in which all medical devices 201 (and their corresponding hosts) within a given geographic area can be remotely analyzed.

One method of the present invention for accomplishing this task of remotely identifying an individual (see FIGS. 6-7) is to take advantage of the fact that each individual medical device 201 has its own unique identification (I.D.) tag 210, which distinguishes it from all others, including devices of the same make, model, and version. One could create different ways in which this I.D. tag 210 can be referenced. As previously discussed, in one exemplary embodiment, the program can obtain data from imaging devices 202 which directly visualize the I.D. tag 210 which is embedded within the device 201 through conventional visualization technologies (e.g., x-ray).

However, in one exemplary embodiment, in the instance where the host subject 213 is remote, direct visualization may not be feasible. In addition, it is also entirely possible that host subject identification requires some degree of secrecy, so that the host in question is unaware of the identification process. An example of such a scenario is when the host subject is attempting to evade detection and as a result, the identification process requires technology which can be performed without active participation (or even awareness) on the part of the host subject.

In one embodiment, while a number of potential signal emissions can be used for remote identification, at the present time, the optimum one is radiofrequency (RF) signals, since these provide for long distance travel and reliable transmission. If each medical device is designed to transmit its own unique I.D. tag 210 into an RF signal on a routine basis (e.g., once every minute), then a remote device 211 such as a drone or satellite could receive and the program can analyze the incoming RF signals from all transmitting medical devices 201 within a given geographic area and identify these devices 201 based upon the unique I.D. tags 210 contained within these transmitted RF signals.

In one embodiment, a challenge arises when a large population of host subjects are contained within the target geographic area. In one exemplary embodiment, the host subject of interest is believed to be located within a football stadium, in which 60,000 people are in attendance. With no additional knowledge as to the potential location of the targeted host subject, all emitted RF signals containing their I.D. tags 210 must be received, analyzed, and localized by the program (i.e., detectors 203, identification module 204, visualization map module 205) in real-time, requiring the artificial intelligence module 207 to assist in the large pool of data being received.

In one embodiment, since each device 201 is transmitting these RF signals at a predictable and regular rate, as the data is processed by the program, there is ample opportunity to continuously narrow and fine tune the search. In addition, if multiple signal receivers 211 (e.g., drones) are available to receive, and in this case, analyze, and localize the devices (and their corresponding host subjects) (via detectors 203, identification module 204, visualization map module 205), then the signals can undergo triangulation by the program for enhanced localization. Once the device 201 of interest has been definitively localized by the program, then the identified host 213 can become the subject of additional in-depth analysis through continued surveillance and use of additional identification tools (as will be subsequently described in further detail) for enhanced confirmation of identity.

In one embodiment, another possible strategy for remote identification is through remote device 201 tracking through the incorporation of embedded microchips 212 in the device which would be analogous to GPS tracking. If these embedded microchips 212 possess the capability of being selectively turned on and off by authorized third parties when a given host subject or device requires localization, the microchips in the device of interest can be selectively activated by the program. This provides a highly selective method for identifying a given host subject within a large geographic and densely inhabited area.

In one embodiment, once the embedded microchips 212 are activated and localized by the program, additional device-specific identifiers can be deployed by the program (e.g., device transmission profile), to serve as a method for authenticating the specific device 201 and host subject 213. For security purposes, any third-party requesting activation of the device embedded microchip 212 would first be required to go through their own authentication process, to ensure they had the appropriate credentials and authorization for such an action. In addition, activation of the device tracking system would automatically trigger an alert and audit by the program of the device database 206.

In one embodiment, in addition to geospatial localization, the program of the device embedded microchip 212 can track locational change of the device 201 in vivo. In one exemplary embodiment, an implanted device 201 (e.g., intravascular filter) becomes detached from its desired anatomic location (e.g., inferior vena cava) and begins to migrate within the bloodstream. In such an occurrence, the embedded microchip 212 may become automatically activated by the presence of device 201 movement (e.g., through embedded accelerometers or ultrasound motion sensors). Once activated, the embedded microchips 212 will continuously track in vivo 4-dimensional (4D) locational change of the device 201. If the locational change of the device 201 in question was to exceed a predetermined threshold (as defined in the device database 206), an automated triggering mechanism could be activated by the program which would send an automated alert to authorized third parties for evaluation and potential intervention.

In the exemplary embodiment an IVC filter which becomes detached from its intended anatomic location and begins to migrate within the bloodstream, the embedded motion sensors 214 within the device 201 would detect unwarranted device movement, which in turn would be provided to the program for analysis, and which would cause the program to activate the embedded microchip 212 for locational tracking. At the same time, an automated alert would be sent by the program to the authorized healthcare providers in order to engage them in any required intervention.

In one embodiment with respect to the remote tracking capability of the embedded microchip 212, an automated activation pathway can also be triggered by the program in the event that the host subject 213 was to travel beyond a predefined geographic area (similar to the automated signal for in vivo device movement). In this example, suppose a host subject is assigned to a limited geographic location for security or health reasons. Examples may include a prisoner, hospital patient, or elderly host with mental impairment (e.g., dementia). In the event that the host subject 213 was to travel beyond the defined geographic area, the internal tracking mechanism of the device 201 could be automatically activated by the program, and the tracking feature engaged by the program. Authorized third parties can be sent notifications and updates of the host subject 213 location by the program, in the event that intervention is deemed required by the program.

In one embodiment, another application of the device internal tracking system is when a host subject 213 becomes physically or mentally impaired and is in immediate danger. Suppose for example, real-time data inputted from any one of a number of sensors 214 of the medical devices 210, which are analyzed by the program, determines that the host subject 213 is in immediate danger (based on a variety of threshold issues pre-programmed into the medical device 201). This may include, for example, a pacemaker lead breakage (i.e., data stops being inputted from the lead), an occluded vascular stent, or a malfunctioning ventriculostomy tube (i.e., data changes or stops being received, etc.). Alternatively, the patient may have incurred severe trauma and triggers the automated alert themselves by a remote device (i.e., remote control, or keyed input). Regardless of the circumstances, any one of these events could have the program automatically trigger the device locational tracking system which would allow identification and localization of the host subject 213 by the program, as well as automated notification issued by the program via electronic methods (i.e., electronic communication devices 215 such as fax, pager, email etc.) to authorized third parties for required intervention.

To summarize, in one embodiment, remote device localization and host subject identification can be performed in a variety of ways, including RF signals transmitting the unique device I.D. tags and selective activation by the program of internally embedded microchips.

In one embodiment, another potential method for remote host subject identification and device localization is through remote sensing technologies 216. Traditionally, remote sensing technologies 216 are used for physical environmental applications (e.g., geology, oceanography), where energy in the form of electromagnetic radiation, RADAR, or LIDAR are emitted and received by remote sensors. If medical devices 201 can be sensed based upon various types of energy emissions (which can be directly incorporated into medical device design and functionality), then remote sensing and visualization technologies (i.e., remote sensing technologies 216, processor 200) incorporated into the remote devices 216 (e.g., satellites, drones, CCTVs) can identify those individuals remotely through device-specific energy emissions.

In one embodiment, this method of remote device identification based upon analysis of emitted energy is by recording the attributes of energy emission for each individual device 201 within the device database 206. At the same time, device manufacturers can incorporate energy emission protocols and standards into device design, so that given device model and version would have a predictable patterns of energy emission, which can serve as a trackable method for remote identification.

In one embodiment, as more and more medical devices 201 incorporate smart technology into their design and functionality, miniaturized computers 217 embedded within the devices 201 provide another method for identification and authentication, based upon the characteristics of their signal transmissions, which can be referred to as the "device transmission profile", In one embodiment, a number of variables can be used by the program to create a "transmission profile" for both the entire device 201, as well as its various subcomponents. These variables can include (but are not limited to) physical attributes of the transmissions (e.g., radiofrequencies, signal patterns), data being exchanged (e.g., data format, context, volume), and security features (e.g., encryption, de-encryption, codes).

In one embodiment, the ultimate goal is for these device-specific transmission profiles to be unique enough so that the program differentiates one similar smart medical device 201 from another, as in the example of two vascular stents created by the same manufacturer. By the program cataloguing each device's signal transmission profile into the device database (not shown), the program can identify and/or authenticate a given medical device 201 based on these signal transmissions.

In one embodiment, the transmissions of smart medical devices 201 can be analyzed by the program on an individual and/or grouped basis. As medical devices continue to evolve, inter-device communication will become more commonplace. As a result, another method for device identification includes inter-device communication and data analysis.

In one embodiment, inter-device communication occurs in a variety of situations including (but not limited to) devices 201 entirely within the host subject 213, devices 201 both internal and external to the host subject 213, and devices 201 between different hosts 213. An example of the latter may include that of a brittle diabetic patient, whose in vivo insulin pump communicates with a wearable smart device 201 of his/her healthcare provider, thereby allowing for real-time data transfer and communication between patient and physician, which facilitates rapid real-time fine tune adjustments by the program of the insulin pump parameters.

In one embodiment, this ability of smart medical devices 201 to communicate with one another may be continuous, semi-continuous, periodic, conditional, sporadic, ad hoc, or emergent. The various parameters which define these inter-device communications can be an extension of each individual device's transmission profile or serve as an independent and standalone unique device identifier. Variables which can be contained within the inter-device communication profile may include (but are not limited to) device codes, transmission frequencies, timing and duration of communications, type, context, and volume of data exchange, security features, communication protocols, and emergency override or shut down procedures.

In one embodiment, anatomic positioning may also serve as a device-specific identifier, albeit in a secondary role. Depending upon the host subject anatomy and manner in which the device 201 was originally placed, subtle differences in anatomic positioning may be determined by the program. In addition, underlying pathology may serve as a cause for device 201 positional change, such as in the example of a biliary duct stent which may be displaced in the presence of underlying malignancy. When these deviations in device positioning are consistent and reproducible over time, they may serve as a device 201 identifier which the program can detect, analyze and report.

In one embodiment, device 201 anatomic location may also be relevant when host anatomic variations are present, and since these remain fixed over time, their intrinsic value in device identification is significant. In one exemplary embodiment, a host subject's left renal artery stent is being used for identification/authentication purposes by the program. This particular individual has a commonly encountered anatomic variation of two left renal arteries (instead of the more common single renal artery). The left renal artery stent which was inserted to treat renal artery stenosis was positioned in the dominant left renal artery, which is cephalad (i.e., superior) with respect to the second left renal artery. By incorporating the anatomic location of the left renal artery stent into the identification schema, the accuracy can be enhanced, since this particular anatomic variation is seen in only 20% of the overall population.

Unlike biometrics, in which an individual biologic trait or characteristic is distinct and unrelated to other traits, medical devices 201 frequently have a number of associated or secondary variables (like anatomic position), which can serve as identifiers in both isolation or in combination with the device primary identifying variables (e.g., device type, manufacturer, model number). As a result, medical devices 201 naturally create multi-factor identification/authentication schema, providing the program with increased sensitivity and specificity, when compared to single factor authentication.

In one embodiment, a secondary device identifying variable is device 201 functionality. In the future, medical devices 201 will frequently transition from single function devices (e.g., vascular catheter for venous access) to multi-function devices (e.g., vascular catheter with embedded biosensors and miniaturized components with capabilities of venous access, drug infusion, tissue sampling, and bioassay). With expanded functionality, comes greater device differentiation.

In one embodiment, device functionality is analyzed in a variety of ways by the program including (but not limited to) device architecture, subcomponents, data (which can be created, stored, analyzed, and transmitted at the device level), movement (including motion), independent actions, and interactions with other devices. In some circumstances, devices with the same make and model number can differ based upon their functionality, which becomes a point of distinction and unique identification.

In an exemplary embodiment, two identical common bile duct stents 201 are present in different host subjects 213. In the first subject, the stent has been placed to provide patency across a stenotic (i.e., narrowed) common bile duct due to pancreatitis. In the second subject, the common duct stent has been placed to provide patency for a common bile duct which has been obstructed by tumor (i.e., cholangiocarcinoma). While both common duct stents are the same make and model and contain the same subcomponents, the second duct stent has activated infusion ports for dispensing chemotherapy, while the first stent's infusion ports are inactive. By the program identifying differences in functionality, the host subjects of these two structurally identical common bile duct stents can be differentiated from one another.

In one embodiment, devices 201 can undergo modification through the incorporation of miniaturized components into the native device architecture, thereby expanding functionality. As previously discussed, data specific to each medical device 201 can be recorded into a standardized device database (not shown), which can serve as a valuable resource for host identification. But the same type of data can also be recorded for device subcomponents (not shown), which may be incorporated at the time of original device manufacture or at a later date. At the time each device is inserted, the corresponding device (and subcomponents) data can be recorded by the program into a master device database which records a number of mandatory and elective data elements including (but not limited to) those listed above, such as:

1. Primary Device (Manufacturer Name, Model, Version, Identification Number, Manufacturer Location, Manufacture Date, Expiration Date, FDA Data [if applicable]).
2. Secondary Devices (Same as Primary Device).
3. Implementation (Provider Name/s, Location, Institution (if applicable), Date and Time, Anatomic Location, Complications (if applicable).
4. Host (Name, Demographic Data, Clinical Indication, Primary and Secondary Diagnoses, Authorized Clinical Providers, Emergency Contact/s, Medical/Surgical History, Other Devices).
5. Functionality (Anatomic Location, Positional Variability, Transmission Profile, Communication Protocols, Security Features, Quality Assurance and Control, Pertinent Data).
6. Related Devices (Same as Primary Device, Data Exchange, Anatomic Location/s, Communication Protocols).
7. Visualization (Imagery, Device Architecture [Roadmap], Signal Output, Functional Analysis).

In one embodiment, the data can in turn be stored by the program in a series of local, regional, national, and/or international databases 206, 208 along with linkage to the host subject's electronic medical record and manufacturer device databases 208. This provides an accessible patient and device-specific resource which can be readily used by the program for both device and host identification/authentication. In circumstances when a host patient's medical/surgical history, anatomy, and/or pathology is relevant, the linkage of data contained within the patient's electronic medical record can prove to be a valuable ancillary resource, since medical device identification may be intrinsically related to host patient health status and/or anatomy.

In one embodiment of the present invention, the combination of device-specific data and patient medical data can create unique identifiers which go beyond device-specific data alone and add increased specificity for host identification. In the previous cited example of two different patients with the same type of biliary duct stent, the additional medical data related to their underlying conditions (pancreatitis in one, cholangiocarcinoma in the other), can serve as distinct device identifiers, which the program can use to uniquely identify each individual host, despite the fact that they essentially have the same device.

In one embodiment, another important device identifier is structure, which also encompasses structural integrity and structural plasticity. Just as in biometrics, where senescence or trauma can change biometrics markers, the same can occur with medical devices 201. A given device begins its lifetime in a relative state of fixed and unblemished structure, which is nearly identical to devices of similar make, model, and version. Over time, however, devices can undergo structural change due to a host of physical and technical factors, which may ultimately produce structural change in the medical device.

In one embodiment, a commonly encountered example of structural change is seen in orthopedic and spinal devices, such as pedicle screws in the post-operative spine and joint prostheses. With constant changes in body mechanics and advancing age, a number of structural changes, breakage, or shift in positioning can occur in these embedded devices. When these structural and/or positional changes are documented, these can serve as unique identifiers, which are specific to the individual host subject and medical device 201. In addition to these device structural changes, the surrounding anatomic structures may also undergo change, which can also serve as unique identifiers. One such common example is localized bony hypertrophy which occurs with prolonged stress adjacent to the device, which can be readily visualized and documented through the use of conventional medical imaging technologies.

Up until now, the discussion of medical device identification and authentication has largely focused on medical devices as single, standalone items. In reality, medical devices often act in synergy with one another, and this phenomenon of multi-device interaction will likely increase in the future. Relevant examples of multi-device interaction are discussed in the patent applications above that are incorporated by reference. As real-time data collection, analysis, and intervention drives healthcare in the future, smart medical devices will be at the forefront and will necessitate the ability to communicate data with one another. The integration of microprocessors and computing capabilities within in vivo medical devices will facilitate intra and inter-device data analysis and communication.

While current medical device technology largely acts independently, the present invention encompasses medical devices 201 that possess the ability to act in a synergistic fashion, so that multiple devices 201 may act in concert with one another to expand diagnostic and therapeutic capabilities. Take for example a patient with longstanding cardiac disease who suffers from both coronary artery disease and cardiac arrythmias. As a result, this patient has a number of implanted devices which include an AICD, cardiac loop recorder, and coronary artery stents. While any single device 201 can be used for identification/authentication of the patient by the program, in one embodiment, combining two or three devices 201 into the identification process, dramatically increases identification accuracy.

In one embodiment, another potential identification strategy would be for the program to utilize the communication which takes place between these devices 201. Suppose the coronary artery stent provides routine updates on flow parameters within the coronary artery and this data is in turn communicated by the program to both the AICD and loop recorder and saved by the program in a database 206. If the communication protocols for these inter-device communications is known, in one embodiment, this can also serve as a method for host identification/authentication that can be used by the program.

In one embodiment, at the same time, some inter-device communications may be periodic in nature and not part of a routine and predictable communication protocol. Despite this lack of predictability, inter-device communication may serve as a method for host identification.

In an exemplary embodiment, an unidentified and unconscious patient is found by paramedics in the field. While no identifying data is available, on superficial examination, the paramedics note that the patient has an AICD and cardiac loop recorder, along with surgical scars of prior cardiac bypass surgery. With knowledge of these medical devices, in one embodiment, the paramedics may initiate a search of the master device database 208, inputting the devices 201, known patient data (e.g., gender, age, height weight, and bypass scar), along with the current geographic location. In addition, in one embodiment, the paramedics may be able to discern electrical signals being transmitted between the AICD and cardiac loop recorder. By the program recording a portion of these signals and inputting this communication to the device database 206, in one embodiment, the program can now fine-tune the search and render a preliminary identification for the patient, which can be used by the program and/or the user to access the patient electronic medical record for additional clinical data to assist in triage and intervention.

In the exemplary embodiment, once the patient arrives in the emergency room, a chest x-ray can be obtained, and the device unique identifying tag 210 can be determined by the program for definitive patient identification. But for purposes of emergency identification in the field, inter-device communication can serve as a viable source of preliminary identification.

In the exemplary embodiment, at the same time, in the event of an observed irregularity on cardiac rate and rhythm, the program can transmit an alert to both the AICD and coronary artery stent, warning of a potential cardiac event requiring intervention.

In the exemplary embodiment, in addition to these inter-device communications being transmitted to the patient's electronic medical record by the program, an automated transmission may also be triggered by the program to the appropriate patient healthcare provider, which in this case is his/her cardiologist. Before the cardiologist is provided with access to this transmitted data, they would have to undergo their own authentication process using the program, for security purposes. Once this has been completed, the data being transferred by the program from the patient to the cardiologist is also recorded in both the patient electronic medical record 208 and device database 206 by the program. All corresponding devices 201 would be documented by the program, which in this case would also include the cardiologist receiving device (e.g., smart watch).

In the exemplary embodiment, if the paramedics in the field have documented an emergent clinical situation requiring feedback from all involved individuals, the transmitted data by the program from the unidentified patient to the cardiologist would incorporate this emergency request. The cardiologist would be provided by the program with contact information for the emergency personnel and direct communication could then proceed. Once the emergency personnel are in direct communication with the cardiologist, patient identification could be provided by the cardiologist, representing another method of patient identification. Once received, the emergency personnel could access the patient's electronic medical record and confirm the patient's identity, along with gaining access to valuable patient healthcare data to assist in the triage and treatment processes.

The above exemplary embodiment illustrates how inter-device communications of both patients and authorized healthcare providers can be used for identification/authentication. All data being accessed, recorded, and transmitted by the program is documented in the corresponding device and healthcare databases 206, 208 by the program, for review and auditing.

In one embodiment, the same principles can also be applied to device subcomponents (i.e., computer processor 217 having modules 204-207, embedded microchips 212, activation sensor etc.), which can be thought of as individual devices contained within a larger host device 201. Each of these individual device subcomponents (e.g., microprocessors, biosensors, miniaturized devices) can serve as unique identifiers in structure, form, and functionality. In the same manner that one device may communicate with another device, so too can individual device subcomponents.

In one embodiment, another method for device identification and authentication is the quality assurance (QA) and quality control (QC) testing, which is (or should be) a fundamental requirement for all medical devices, in order to ensure reliability, accuracy, and security of operation. Some of the various methods for routine QA/QC testing was described in the above patents that are herein incorporated by reference.

In one embodiment, the present invention is unique and relevant as the medical device QA/QC testing can serve as a unique identification method, for despite the fact that devices can be of the same manufacturer, model, and version; they may have entirely different and unique QA/QC test results, making each device unique from its counterparts.

In one embodiment, when a given QA/QC deficiency is documented, consistent, and reproducible; this creates an opportunity for the present invention to use this specific quality deficiency as a device identifier, in the same way that a specific medical device structural defect can also serve as a unique identifier. In an exemplary embodiment, a smart vascular catheter contains a number of subcomponents, including a variety of biosensors which are used for chemical assays in the blood. One of these biosensors has been identified as being malfunctioning on routine QA/QC testing by the program, and as a result has been remotely shut down (i.e., turned off) by the program and/or the user pending replacement.

In the exemplary embodiment, with documentation of this QC deficiency and knowing the exact location of this deficient biosensor relative to overall medical device architecture, this can serve as a unique device identifier to the program. The non-operational biosensor can be identified and cross-referenced by the program with the device specific QA/QC reports in the device database 206 to identify and authenticate the device 201 and its host subject 213. In this respect, ongoing QA/QC deficiencies may indirectly have a positive impact, in their ability to serve as unique device identifiers.

In one embodiment, since medical device security is of fundamental importance to operational performance and patient safety, numerous security features and methods have been described and will continue to evolve in the future. While there are various methods used for device security, the following list some relevant methods on how device security can be used as a device identifier.

In one embodiment, depending upon the various types of hardware and software employed, these security features can in themselves serve as device identifiers. While the specifics of these security features would remain hidden to unauthorized individuals, authorized operators with access to the security could potentially use these for the purpose of device identification and authentication.

In one embodiment, given the large amount of data generated in the creation of a device database 206 and the requirement for rapid and accurate real-time identification/authentication, artificial intelligence (AI) (i.e., AI module 207) will play an important role in the present invention. A more detailed discussion of AI in smart devices was described in the patents incorporated by reference above. A key point to be made is that as the device database 206 expands in breadth and depth, the expansive quantity of device-related data will lend itself to a wide array of AI applications. One of these is the ability to provide statistical probabilities for the various device identifiers used in the invention, which can be used by the program for iterative refinement of the device identifiers and their resulting analytics.

In one embodiment, a variety of artificial intelligence techniques can be adapted to the present invention including (but not limited to) machine learning to mine, search, and analyze large datasets, automated identity verification, convoluted neural networks and feature extraction for automated image processing, and calculation of statistical probabilities in the identification/authentication process.

In one embodiment, with the abundance and diversity of objective and standardized data attributable to medical devices and their increasing utilization in the general population, medical devices can provide a novel and potentially superior approach to identification and authentication, when compared with conventional strategies.

In one embodiment, the present invention is implemented via a complex series of ordered steps in the Medical Device Identification/Authentication Process, which includes for various scenarios (embodiments):

1. Non-communicative burn victim presents to emergency room (ER) (see FIG. 3).
2. Non-accessible device database for non-communicative burn victim who presents to the ER (see FIG. 4).
3. No I.D. tag for non-communicative patient in the ER (see FIG. 5).
4. Remote identification of known individual (i.e., terrorist with known identity preparing an attack within large crowd) (see FIG. 6).
5. Remote identification of multiple subjects (i.e., mass casualties resulting from terrorist attack) (see FIG. 7).

In one embodiment, starting with the non-communicative burn victim FIG. 3 scenario, the identification of the burn patient is established by the unique identification (I.D.) tag 210 contained within either one or both of their medical devices 201, which include an automated implanted cardiac defibrillator (AICD) and Mediport catheter.

In step 300, the requesting healthcare provider provides authentication information and is verified by the computer system 100 at the hospital.

In step 301, the patient's name and identifying data (e.g., social security number) is entered into the hospital database 206.

In step 302, the information from the patient's vital signs and cursory physical exam are entered into the hospital database 206 (i.e., left mastectomy, pacemaker, scar on right thigh, third degree burns over entire body).

In step 304, imaging technologies 212 are employed on the patient/host, to identify the unique I.D. tag 212 (e.g., serial number A6GT15042X) of the pacemaker 201. If there is no device I.D. tag 212, or it is unreadable etc., the program goes to the steps in FIG. 5 (below).

In step 304, using at least this device ID tag 212 as a primary identifier (along with a Mediport® catheter), the information on the patient is provided to the identification module 201, which accesses the data storage 206, 208 to locate the patient's name and other identification (e.g., social security number), which is provided to the user 218 (i.e., medical professional) in step 305.

In step 306, once the patient's identification has been confirmed by the identification module 204, the program queries the patient's electronic medical record (EMR) 208 for the dual purpose of validating their identification and retrieving healthcare information which may be assist in diagnosis and treatment planning, along with notification of emergency contacts. In this circumstance, the EMR 208 serves as a secondary identifier, as well as a valuable data resource. Typically, the EMR 208 has the pacemaker I.D. confirmation, and confirms medical (surgical) data, including breast cancer (left mastectomy), documented scar right thigh, and patient data (e.g., gender, ethnicity, height, weight, blood pressure, pulse, etc.).

In step 307, once the corroborated data within the EMR 208 validates the device identifiers (i.e., pacemaker I.D. tag 212) the patient is confirmed as a match, resulting in an identification accuracy in excess of 99%.

If the EMR database 208 is not accessible (step 307) or the patient is not confirmed as a match with the EMR 208 records (step 308), then other scenarios are invoked; namely, FIG. 4 (non-accessible database—same steps as if there is no I.D. tag 212).

In one embodiment, FIG. 4 continues with the scenario that there is a non-accessible device database 206, 208 for the non-communicative burn victim, as determined at step 307 of FIG. 4.

As noted above, this scenario is nearly identical to the scenario of FIG. 3 (steps 300-305), except the device database 206, 208 is non-accessible, requiring an alternative method for identification.

In step 401, using device 201 imagery provided by a standard portable chest x-ray (CXR) 202, the imaging data is provided to the identification module 204 and analyzed by the artificial intelligence module 207 of the processor 200 (e.g., convoluted neural networks, feature extraction), for determination of device-specific attributes.

In step 402, since the device database 206, 208 is non-accessible, the program locates alternative data sources, which can take a variety of forms including (but not limited to) the device manufacturer's databases 219 and regional EMRs 208. By the program inputting data into both the pacemaker and Mediport® catheter manufacturer databases 219, a list of potential patients is established by the program for the user 218.

In step 403, by the program cross-referencing these two lists, a narrowly focused list of patients with both devices is obtained, which can be further reduced based upon geographic location (assuming the patient lives locally). For example, the pacemaker specifics can be searched in the manufacturing database 219, and the search in the regional EMR 208 would include parameters such as patient race/ethnicity, gender, age (range), height, weight, and medical history (i.e., a pacemaker and a left mastectomy).

In step 404, by taking this limited patient list and the program can search respective EMRs 208 or databases 206, such that the correct patient identity can be established by the program, based upon physical exam data (including but not limited to) age, gender, height, weight, and other identifying physical characteristics.

In step 405, the patient identification can be provided to the user.

In the even that further confirmation is required after step 403 or step 404 due to no exact match or strong matches being identified (step 406), secondary device identifiers, such as device structural characteristics, QA/QC data, device transmission profile, and device subcomponents, can be entered into the search parameters of the databases 219, 208, in step 407, and searched in step 404. Collectively, when the patient is identified (step 405), this results in an identification accuracy exceeding 99%.

Figure 5:
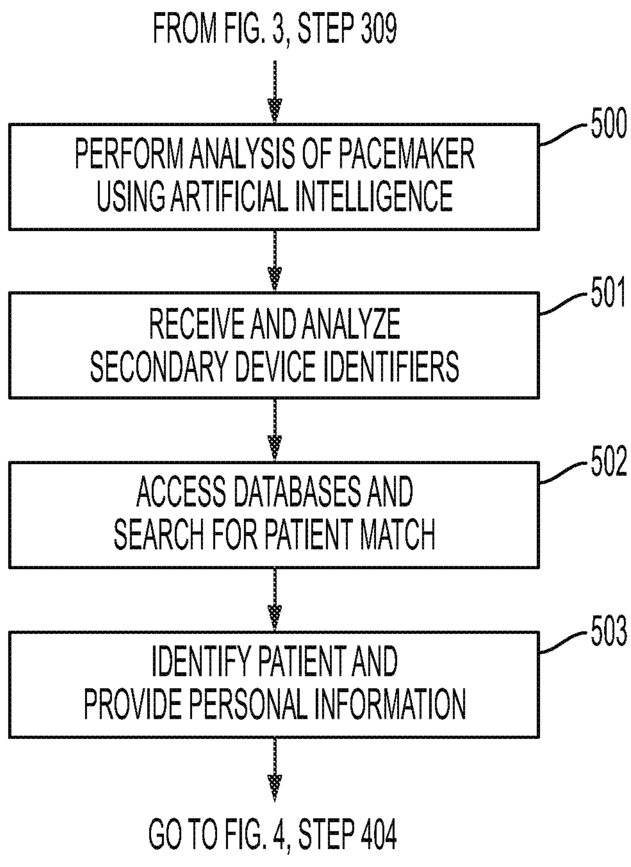
FIG. 5 is a flow chart of a method of identifying a patient identity with no identification (I.D.) tag, according to one embodiment consistent with the present invention.

In one embodiment, FIG. 5 provides a process for where there is an absent, unreadable, or identifiable device I.D. tag (i.e., catheter). This scenario includes identical steps in FIGS. 3 and 4, but only in this example, device-specific I.D. tags 212 are not discernible. While in theory this should never be the case, the example is provided to illustrate the multi-functionality of the invention in the ability to identify/authenticate a given individual based on a myriad of device-specific identifiers and data sources.

In this embodiment, once steps 300-304 of FIG. 3 have failed to result in a patient match due to an unidentifiable device, step 500 is invoked, to perform artificial intelligence analysis of the device 201 using the artificial intelligence module 207 (step 401 of FIG. 4). This provides valuable device-specific identifiers for a search.

Next, in step 501, secondary device identifiers (step 407 of FIG. 4) are inputted in order to assist in identifying the device. These would include transmission profile, functional map, structure (i.e., broken lead) and sub-components. Thus, the information from the artificial intelligence analysis is reinforced and supplemented by an array of secondary device identifiers.

In step 502, this collective data can then be inputted into the device databases 206, 208, 219 for patient identification.

In step 503, the patient is identified, and their personal information provided (i.e., name, social security number) to the user.

The process is completed by steps 404 and 405 of FIG. 4, wherein this information is in turn is used by the program to access the patient EMR 208, which then verifies the patient identity and provides it to the user to assist in further patient management, respectively.

In one embodiment, the process of selective identification of a suspected terrorist within a crowd, is shown in FIG. 6.

In this exemplary embodiment, intelligence has uncovered information of an impending terrorist attack by a known terrorist, with an established identity. The site of the impending attack is an outdoor concert with an estimated attendance of 10,000 people. Given limitations in on the ground security, aerial surveillance via remote sensing technologies 216 (i.e., drones) is used to search for the terrorist in the hope of identifying him before he can initiate the planned attack.

In the exemplary embodiment, with knowledge as to the identity of the terrorist along with a list of his aliases, in step 600, the user initiates a search of an international device database 206, 208 by the program, along with any provided additional general information provided by security intelligence inputted into the search. This information includes name, age, national origin, race/ethnicity, height, weight, scars, and two devices 201 (i.e., pacemaker and insulin pump).

In step 601, the results show that the terrorist has a documented cardiac pacemaker 201 with a known I.D. tag 212 (or code), which information is used to tag the devices and determine transmission profiles.

Since all tagged medical devices emit periodic signals containing their I.D. code, the user/program determines aerial surveillance devices 216 (drones) are useful (step 602), and in step 603, tasks those surveilling drones 216 to sample the emitted radiofrequency (RF) signals emitted by all medical devices 201 within the crowd.

In step 604, once the signal specific to the terrorist's pacemaker is identified by the program as a match to the terrorist's device transmission profile, the location of the terrorist will be determined in step 605, by triangulating the emitted signals using three separate drone signal receivers 216. Upon successful triangulation and localization of the terrorist, a secondary form of identification is required by the program before taking action.

In one embodiment, one method of secondary identification is high resolution imagery. An alternative option for secondary identification is that of infrared lasers which can monitor cardiac rate and rhythm (i.e., heartbeat). Secondary identification is carried out using one of these methods, or other appropriate method, in step 606.

In one embodiment, since smart medical devices 201 may possess emergency shut down features (i.e., broken glass feature described in the patents incorporated by reference), in step 607, this may be used by the program and/or the user to effectively temporarily turn off pacemaker 201 function in the terrorist. This would have the dual benefit of verifying his identity while temporarily incapacitating the terrorist until he can be apprehended (using nonlethal methods).

The above exemplary embodiment illustrates how each medical device's unique I.D. tag 212 and RF emission can be used to remotely identify and locate a host subject 213. As ancillary technologies continue to evolve (e.g., infrared laser, remote high-resolution imagery, remote sensing technologies), these can be utilized as secondary identifiers.

Figure 7:
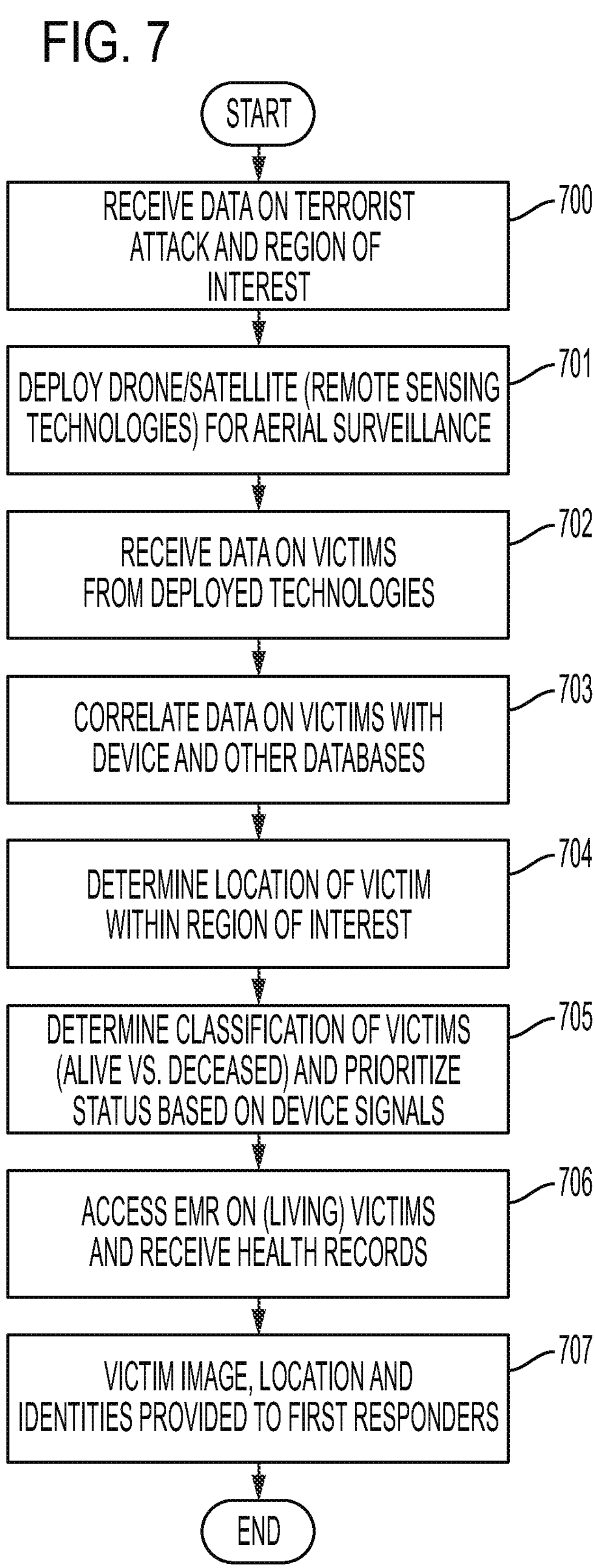
FIG. 7 is a flow chart of a method of remote identification of multiple subjects according to one embodiment consistent with the present invention.

In one embodiment, FIG. 7 shows remote identification and triage of multiple individuals in the setting of mass casualties.

In this exemplary embodiment, in step 700, a terrorist attack was successful, resulting in large number of casualties, and information on the attack provided to government services. If the location of the event was far removed from emergency services or there was an inherent danger limited on the ground response (e.g., radiation from nuclear explosion), then the initial response would be best performed through remote surveillance.

In step 701, just as in the previous example, remote sensing technologies 216 (i.e., drones, satellite, infrared lasers) can be used to survey the extent of damage and provide valuable intelligence for strategic intervention, including video, RF signals, cardiac heartbeats, etc.

In addition to obtaining aerial surveillance and imagery in step 701, in step 702, the drones/satellite(s) can also be used to identify victims based upon each device's RF signal identifier, image recognition, etc.

In step 703, all this information on the victims, is correlated by the program with the relevant databases 206, 208, including device database 219, to reveal each host subject's 213 identity.

In step 704, the location of the identified party/parties 213 can in turn be localized by the program triangulating the received signals from multiple remote sensing technologies (i.e., drones, etc.), just as in the previous example.

However, an important piece of information is knowing which victims remain alive and when are deceased, since this will help direct and prioritize intervention and rescue efforts. Since the device RF signal emissions are independent of patient viability, a remote step and method is required which will accurately discern the living from the deceased victims.

In one embodiment, in step 705, living vs. deceased victims can be identified and prioritized by the program (i.e., alive—highest priority, deceased—low priority, uncertain—intermediate priority). In one embodiment, the program analyzes device signals, and a number of device-specific applications can accomplish the task of identifying and prioritizing victims, including (but not limited to) device functional maps, device transmissions (e.g., bioassays and measurements which are dependent upon active blood flow), and passive device movement (e.g., device positional change caused by active airflow, blood flow).

In step 706, once the living victims have been identified by the program, their respective EMRs can be accessed by the program to provide healthcare data which may be critical in triage and intervention.

In step 707, the (living/priority) victims' images, location, and identities, and health care needs and history, are provided by the program to emergency first responders so that when they enter the area of damage, they can be directed to the individual locations of victims in order of priority, through locational tracking of the victim's device RF signals. Deceased victims information can be provided to coroners' office.

The present invention provides a number of new and novel applications tied to a wide array of medical devices, irrespective of anatomic location, functionality, form, or composition. With the initiation of efforts tied to medical device identification and documentation, one can effectively create technology which can accurately and reliably identify host subjects based upon the medical devices which they possess.

As the functionality, diversity, and complexity of medical devices continues to expand, so does the practicality and efficacy of the invention. This invention offers a number of theoretical and practical advantages of existing identification methods, perhaps the most important of which is the ability to identify subjects without their active participation as well as the ability to perform identification/authentication remotely. It is less a matter of if, but when, such an invention is adopted in everyday life and operation.

As medical devices continue to evolve and become more differentiated in structure, composition, and function; their individual uniqueness will become more pronounced. In some respects, the uniqueness of these devices can be used to define each host subject's unique medical status, and by extension, their identity.

Another unique application of the invention can be created, in which smart medical devices can themselves serve as a primary means of authentication and authorization. As individuals begin to routinely possess smart medical devices, these in vivo smart devices can themselves serve as a means of end-user identification. In essence, each individual person can be defined by the smart medical devices they possess, while the smart medical devices can in turn be defined by the person in which they reside and operate.

In one exemplary embodiment, with the example of a smart cardiac valve prosthesis which has been permanently implanted in the host patient, during the course of its implementation, a number of specific attributes of this smart device were securely recorded by the program in a number of electronic databases, which may include (but not limited to) the medical records of the individual host patient, the device manufacturer, the medical institution of record, and centralized smart device databases.

A variety of data points may be recorded by the program related to this smart device including (but not limited to) the type of device, make and model number, technical specifications, anatomic location, dates of record, operating software (including updates), and applicable medical conditions (for which the device is being used). Since the smart device contains an internal computer processor and memory, and the program running thereon can freely communicate with an authorized external computer system, specific transmission parameters may be used by the program to uniquely identify each individual device. Whenever this active smart medical device is securely communicating with an external computer, the unique signals being transmitted (from either or both devices) can be used by the program to identify both the emitting and receiving smart devices.

This inter-operability can not only be applied between the in vivo smart device and an external computer system, but also between multiple different in vivo smart devices, within a given host patient. In this example of a smart mitral valve prosthesis, inter-device communication achieved by the program may prove to be beneficial with other smart medical devices such as cardiac pacemaker, internal defibrillator, coronary artery stent, or aortic valve prosthesis. Since overall cardiac function is in part dependent upon individual heart components and supporting technologies, it is beneficial for these related smart devices to be in constant communication and coordination of their functions.

Included in the smart device databases will be the unique signal transmission characteristics used by the program which may include (but not limited to) the specific type of energy being used (e.g., light, sound, magnetic field, radiofrequency), the signal frequency, and the transmission pattern (which can be collectively called the "signal transmission profile"). These smart-device signal characteristics can effectively create a unique device-specific identifier, which can be used by the program to identify each individual smart device as well as the host patient in which it resides.

Since it is (or will soon be) fairly commonplace for an individual host patient to possess multiple in vivo smart devices at any one point in time, various combinations of these indwelling smart medical devices can be used for authentication and authorization of the host patient. This in effect will create the biometric equivalent of multi-factor authentication, except in this case it will be multi-device authentication.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A method of identification and localization of a device implanted in a host, or a superficial or wearable device associated with a host, comprising:

providing data on the device to an identification module disposed remote from the host, from at least one of an imaging technology, a visualization technology, a remote sensing technology, or a device identifier;

storing said data in a data storage accessible to the identification module;

analyzing said data using said identification module;

searching one of said data storage or a device database and cross-referencing said analyzed data with said device database; and identifying and localizing at least one of the device or the host using results of said cross-referenced search of said device database.

2. The method of claim 1, further comprising:

preparing a two-dimensional (2-D)/three-dimensional (3-D) visualization map or pictorial representation of the device using a 2-D/3-D visualization module, said 2-D/3-D visualization map which is unique to the host.

3. The method of claim 2, wherein said 2-D/3-D visualization map is provided to said identification module for said cross-referenced search.

4. The method of claim 3, further comprising:

using artificial intelligence (AI) from an AI module to one of prepare said 2-D/3-D visualization map or analyze said data for localization and identification of the device.

5. The method of claim 3, wherein said data storage includes at least one of an internal data storage to the device, an external computer data storage, or an external database; and wherein said external database includes local, regional, and international databases.

6. The method of claim 5, wherein said device identifiers include at least one of: device identification tags, device embedded microchips, device quality assurance (QA)/quality control (QC) testing, device imagery, patient-specific medical data, said 2-D/3-D visualization map, a device motion map, a device transmission profile, inter-device communication, device anatomic location, device functionality, device structural integrity, device individual and/or grouped components, device-specific data, device performance metrics, synergistic devices, or device architecture.

7. The method of claim 1, wherein said imaging technology includes at least one of X-ray, computed tomography (CT), ultrasound, nuclear medicine, or magnetic resonance imaging (MRI).

8. The method of claim 1, wherein said visualization technology includes at least one of thermal, vibration, sound emission, or light measuring technology.

9. The method of claim 6, wherein said device motion map is acquired in real-time and cross-referenced with said device database to identify the device and the host.

10. The method of claim 1, wherein age-adjusted modeling of appearance of the device is performed to predict changes in said device appearance over time.

11. The method of claim 1, wherein remote sensing technologies include at least one of drones, satellites, closed-circuit television (CCTV) or infrared lasers.

12. The method of claim 1, wherein on identification of a targeted host, an internal activation sensor in the device is activated, which emits a signal that is detected by a signal detector and provided to at least one of said identification module or said 2-D/3-D visualization map module.

13. The method of claim 12, wherein said signal includes at least one of laser, ultrasound, electromagnetic radiation, radiofrequency (RF), infrared light, thermal energy, sound, or vibration.

14. The method of claim 6, wherein said device embedded microchips are capable of being selectively turned on and off by authorized third parties when the host or the device requires localization at a large geographic and densely inhabited location.

15. The method of claim 6, wherein identification and localization of the host is implemented on condition that the host travels beyond a predefined geographic area or the host is in imminent danger based on a plurality of predetermined threshold criteria.

16. An apparatus which identifies and localizes a device associated with a host based on a device implanted in the host or a superficial or wearable device associated with the host, comprising:

an identification module disposed remote from the host, which receives data on the device from at least one of an imaging technology, a visualization technology, a remote sensing technology, or a device identifier;

a data storage accessible to the identification module, which stores said data;

wherein said identification module analyzes said data using said identification module, and cross-references said analyzed data with a device database; and wherein at least one of the device or the host is at least one of identified or localized using results of said cross-referenced search of said device database.

17. A method of identifying a patient based on a device implanted in the patient or a superficial or wearable device associated with the patient, comprising:

receiving data from a device by at least one of an imaging technology, a visualization technology, a remote sensing technology, or a device identifier;

obtaining personal identifying information of the patient and storing said identifying information in a data storage;

receiving medical data on the patient from a patient examination;

providing said data from the device and medical data from the patient to an identification module disposed remote to the patient, which accesses said data storage and locates identification data on the patient;

providing said identification data on the patient to a user;

accessing an electronical medical record (EMR) on the patient to validate said identification of the patient and to retrieve patient medical records;

corroborating said identification of the patient with said patient medical records at said identification module; and confirming said identification of the patient.

18. The method of claim 17, wherein on condition that said EMR is not accessible, at least one of an imaging technology, a plurality of alternative databases, or secondary device identifiers are utilized to provide information to said identification module in place of patient medical records; and wherein artificial intelligence is used by an artificial intelligence module to analyze said information and confirm said identification of the patient.

19. A method of identifying at least one individual at a remote location based on a device implanted in the at least one individual, or a superficial or wearable device associated with the at least one individual, comprising:

searching a region of interest for signals emitted by the device associated with the at least one individual, using at least one of an imaging technology, a visualization technology, a remote sensing technology, or a device identifier;

matching said signals emitted from the device with said identifying data on the device at an identification module disposed remote from the individual;

determining a location of the at least one individual based on said signals emitted from the device using said identification module;

implementing a secondary form of identification of the at least one individual including at least remote sensing technologies or visualization technologies; and confirming said identification and said location of the at least one individual.

20. The method of claim 19, wherein an identification of the at least one individual is predetermined, and information on the at least one individual and the device are obtained and used in said searching step.

21. The method of claim 19, wherein the at least one individual is a plurality of individuals.

22. The method of claim 21, wherein said identification module analyzes said signals of said plurality of individuals and distinguishes a status between alive and deceased individuals based on signal from the device, and prioritizes intervention on alive individuals.

23. The method of claim 22, wherein EMRs are obtained on said plurality of individuals and provided to healthcare providers along with location and identification of said alive individuals.

* * * * *